(12) United States Patent
Rioux

(10) Patent No.: US 11,786,295 B2
(45) Date of Patent: *Oct. 17, 2023

(54) ELECTROSURGICAL TISSUE AND VESSEL SEALING DEVICE

(71) Applicant: Innoblative Designs, Inc., Chicago, IL (US)

(72) Inventor: Robert F. Rioux, Ashland, MA (US)

(73) Assignee: Innoblative Designs, Inc., Chicago, IL (US)

(*) Notice: Subject to any disclaimer, the term of this patent is extended or adjusted under 35 U.S.C. 154(b) by 312 days.

This patent is subject to a terminal disclaimer.

(21) Appl. No.: 17/170,428

(22) Filed: Feb. 8, 2021

(65) Prior Publication Data

US 2021/0236196 A1    Aug. 5, 2021

Related U.S. Application Data

(63) Continuation of application No. 15/802,760, filed on Nov. 3, 2017, now Pat. No. 10,912,602.

(Continued)

(51) Int. Cl.
*A61B 18/14*    (2006.01)
*A61B 18/00*    (2006.01)

(52) U.S. Cl.
CPC .. *A61B 18/1445* (2013.01); *A61B 2018/0013* (2013.01); *A61B 2018/00029* (2013.01);
(Continued)

(58) Field of Classification Search
CPC ...... A61B 18/1445; A61B 2018/00029; A61B 2018/00083; A61B 2018/0013;
(Continued)

(56) References Cited

U.S. PATENT DOCUMENTS 4,205,668 A    6/1980 Criddle
4,699,147 A    10/1987 Chilson et al.
(Continued)

FOREIGN PATENT DOCUMENTS

CN    2610858 Y    4/2004
CN    104546124 A    4/2015
(Continued)

OTHER PUBLICATIONS

Final Rejection issued in U.S. Appl. No. 16/876,284, dated Aug. 12, 2022, 14 pages.
(Continued)

*Primary Examiner* — Michael F Peffley
(74) *Attorney, Agent, or Firm* — Brown Rudnick LLP; Matthew P. York

(57) ABSTRACT

An electrosurgical device can be delivered to a tissue site to provide supplemental sealing of vessels and/or vascular tissue that include suturing, stapling, or the like. The electrosurgical device is generally in the form of forceps, and includes an end effector assembly including opposing movable jaws. Each jaw includes a deformable pad or cushion including an electrode array positioned thereon. Each deformable cushion is configured to deliver a fluid, such as saline, during activation of the electrode array, thereby creating a virtual electrode which couples radiofrequency (RF) energy emitted from the electrode array into tissue in which the RF energy is converted into thermal energy. The deformable cushion and electrode array provide a controlled degree of compression upon the target tissue or vessel to maintain integrity of a suture, staple, or clip, as well as controlled energy emission for sealing, cauterizing, coagulating, and/or desiccating the target tissue or vessel.

20 Claims, 8 Drawing Sheets

Related U.S. Application Data

(60) Provisional application No. 62/419,227, filed on Nov. 8, 2016.

(52) U.S. Cl.
CPC ............ *A61B 2018/0063* (2013.01); *A61B 2018/00083* (2013.01); *A61B 2018/00577* (2013.01); *A61B 2018/00589* (2013.01); *A61B 2018/00595* (2013.01); *A61B 2018/00607* (2013.01); *A61B 2018/145* (2013.01); *A61B 2018/1465* (2013.01); *A61B 2018/1472* (2013.01); *A61B 2218/002* (2013.01)

(58) Field of Classification Search
CPC .. A61B 2018/0057; A61B 2018/00589; A61B 2018/00595; A61B 2018/00607; A61B 2018/0063; A61B 2018/145; A61B 2018/1465; A61B 2018/1472; A61B 2218/002

See application file for complete search history.

(56) References Cited

U.S. PATENT DOCUMENTS

| | | |
|---|---|---|
| 4,976,711 A | 12/1990 | Parins et al. |
| 4,979,948 A | 12/1990 | Geddes et al. |
| 5,015,243 A | 5/1991 | Schifano |
| 5,045,056 A | 9/1991 | Behl |
| 5,052,411 A | 10/1991 | Schoolman |
| 5,100,423 A | 3/1992 | Fearnot |
| 5,117,828 A | 6/1992 | Metzger et al. |
| 5,127,411 A | 7/1992 | Schoolman et al. |
| 5,159,921 A | 11/1992 | Hoover |
| 5,163,938 A | 11/1992 | Kambara et al. |
| 5,211,639 A | 5/1993 | Wilk |
| 5,334,193 A | 8/1994 | Nardella |
| 5,429,605 A | 7/1995 | Richling et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,688,270 A * | 11/1997 | Yates ............ A61B 18/1447 606/49 |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,647 A | 4/1999 | Mochizuki |
| 5,893,847 A | 4/1999 | Kordis |
| 5,913,855 A | 6/1999 | Gough et al. |
| 5,928,229 A | 7/1999 | Gough et al. |
| 5,935,123 A | 8/1999 | Edwards et al. |
| 5,941,873 A | 8/1999 | Korenfeld |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,113,598 A * | 9/2000 | Baker ............ A61B 18/1445 606/51 |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,315,776 B1 | 11/2001 | Edwards et al. |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,663,622 B1 | 12/2003 | Foley et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,770,072 B1 * | 8/2004 | Truckai ............ A61B 18/1445 606/49 |
| 6,780,183 B2 | 8/2004 | Jimenez, Jr. et al. |
| 6,805,131 B2 | 10/2004 | Kordis |
| 6,826,421 B1 | 11/2004 | Beally et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,942,650 B1 | 9/2005 | Schultz et al. |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,311,708 B2 | 12/2007 | McClurken |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,507,234 B2 | 3/2009 | Utley et al. |
| 7,507,238 B2 | 3/2009 | Edwards et al. |
| 7,530,979 B2 | 5/2009 | Ganz et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |

(56) References Cited

U.S. PATENT DOCUMENTS

| | | |
|---|---|---|
| 7,803,156 B2 * | 9/2010 | Eder ................ A61B 18/1442 606/51 |
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan et al. |
| 7,959,627 B2 | 6/2011 | Utley et al. |
| 7,959,628 B2 | 6/2011 | Schaer et al. |
| 7,959,631 B2 | 6/2011 | DiCarlo |
| 7,993,336 B2 | 8/2011 | Jackson et al. |
| 7,997,278 B2 | 8/2011 | Utley et al. |
| 8,012,149 B2 | 9/2011 | Jackson et al. |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 | 7/2012 | de la Rama et al. |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,518,018 B2 | 8/2013 | Minskoff et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 | 3/2015 | Woloszko et al. |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 10,070,921 B2 | 9/2018 | Rioux et al. |
| 10,470,818 B2 | 11/2019 | Rioux et al. |
| 10,786,305 B2 | 9/2020 | Mahvi et al. |
| 11,083,519 B2 | 8/2021 | Rioux et al. |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2002/0120259 A1 | 8/2002 | Lettice et al. |
| 2002/0120267 A1 | 8/2002 | Phan |
| 2002/0128641 A1 | 9/2002 | Underwood et al. |
| 2003/0009166 A1 | 1/2003 | Moutafis et al. |
| 2003/0036680 A1 | 2/2003 | Black |
| 2003/0079309 A1 | 5/2003 | Vandenbelt et al. |
| 2003/0130711 A1 | 7/2003 | Pearson et al. |
| 2003/0163128 A1 | 8/2003 | Patil et al. |
| 2003/0216725 A1 | 11/2003 | Woloszko et al. |
| 2003/0225403 A1 | 12/2003 | Woloszko et al. |
| 2003/0233099 A1 | 12/2003 | Danaek et al. |
| 2004/0049165 A1 | 3/2004 | Thompson et al. |
| 2004/0087936 A1 | 5/2004 | Stern et al. |
| 2004/0092960 A1 | 5/2004 | Abrams et al. |
| 2004/0122352 A1 | 6/2004 | John |
| 2005/0004535 A1 | 1/2005 | Schklair |
| 2005/0049454 A1 | 3/2005 | Ouchi |
| 2005/0054993 A1 | 3/2005 | Falahee |
| 2005/0059965 A1 | 3/2005 | Eberl et al. |
| 2005/0070894 A1 | 3/2005 | McClurken |
| 2005/0154386 A1 | 7/2005 | West et al. |
| 2005/0187491 A1 | 8/2005 | Burbank et al. |
| 2006/0069385 A1 | 3/2006 | Lafontaine et al. |
| 2006/0212032 A1 | 9/2006 | Daniel et al. |
| 2006/0259027 A1 | 11/2006 | Kwan et al. |
| 2007/0083195 A1 | 4/2007 | Werneth et al. |
| 2007/0100201 A1 | 5/2007 | Komiya et al. |
| 2008/0004534 A1 | 1/2008 | Gelbart et al. |
| 2008/0015565 A1 | 1/2008 | Davison |
| 2008/0103494 A1 | 5/2008 | Rioux et al. |
| 2008/0140001 A1 | 6/2008 | Globerman et al. |
| 2008/0234673 A1 | 9/2008 | Marion et al. |
| 2009/0171340 A1 | 7/2009 | Young |
| 2009/0177193 A1 | 7/2009 | Wang et al. |
| 2009/0248021 A1 | 10/2009 | McKenna |
| 2009/0292177 A1 | 11/2009 | Eggers et al. |
| 2009/0299355 A1 | 12/2009 | Bencini et al. |
| 2010/0114087 A1 | 5/2010 | Edwards et al. |
| 2010/0256629 A1 | 10/2010 | Wylie et al. |
| 2010/0292689 A1 | 11/2010 | Davison et al. |
| 2010/0330893 A1 | 12/2010 | Turner et al. |
| 2011/0172485 A1 | 7/2011 | Lubock |
| 2011/0257646 A1 | 10/2011 | Utley et al. |
| 2012/0029510 A1 | 2/2012 | Haverkost |
| 2012/0029511 A1 | 2/2012 | Smith et al. |
| 2012/0059437 A1 | 3/2012 | Shalev |
| 2012/0109250 A1 | 5/2012 | Cates et al. |
| 2012/0172680 A1 | 7/2012 | Gelfand et al. |
| 2012/0271253 A1 | 10/2012 | Schultz |
| 2012/0289776 A1 | 11/2012 | Keast et al. |
| 2013/0030425 A1 | 1/2013 | Stewart et al. |
| 2013/0085493 A1 | 4/2013 | Bloom et al. |
| 2013/0109924 A1 | 5/2013 | Gan |
| 2013/0131649 A1 | 5/2013 | Hughett, Sr. et al. |
| 2013/0158536 A1 | 6/2013 | Bloom |
| 2013/0172870 A1 | 7/2013 | Germain et al. |
| 2013/0184702 A1 | 7/2013 | Neal, II et al. |
| 2013/0184706 A1 | 7/2013 | Gelbart et al. |
| 2013/0253506 A1 | 9/2013 | Rioux et al. |
| 2013/0274728 A1 | 10/2013 | Kapur et al. |
| 2013/0310833 A1 | 11/2013 | Brown et al. |
| 2013/0338662 A1 | 12/2013 | Weber |
| 2014/0018788 A1 | 1/2014 | Engelman et al. |
| 2014/0018794 A1 | 1/2014 | Anderson et al. |
| 2014/0031810 A1 | 1/2014 | Mahvi et al. |
| 2014/0039491 A1 | 2/2014 | Bakos et al. |
| 2014/0058343 A1 | 2/2014 | Schultz |
| 2014/0058376 A1 | 2/2014 | Horn et al. |
| 2014/0180273 A1 | 6/2014 | Nair |
| 2014/0221998 A1 | 8/2014 | Latterell |
| 2014/0228801 A1 | 8/2014 | Keeling |
| 2014/0276731 A1 | 9/2014 | Voegele et al. |
| 2014/0276748 A1 | 9/2014 | Ku et al. |
| 2014/0296842 A1 | 10/2014 | Mansi et al. |
| 2014/0378960 A1 | 12/2014 | Fischer et al. |
| 2015/0018817 A1 | 1/2015 | Willard |
| 2015/0141982 A1 | 5/2015 | Lee |
| 2015/0306361 A1 | 10/2015 | Feig et al. |
| 2016/0015444 A1 | 1/2016 | Wittenberger |
| 2016/0045197 A1 | 2/2016 | Mitelberg et al. |
| 2016/0113707 A1 | 4/2016 | Sahakian et al. |
| 2016/0113708 A1 | 4/2016 | Moss et al. |
| 2016/0117221 A1 | 4/2016 | Nair et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1 | 5/2017 | Rioux et al. |
| 2017/0172646 A1 | 6/2017 | Patel et al. |
| 2017/0215947 A1 | 8/2017 | Rioux et al. |
| 2017/0215951 A1 | 8/2017 | Wang et al. |
| 2017/0252092 A1 | 9/2017 | Rioux et al. |
| 2017/0281255 A1 | 10/2017 | Babini et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0076336 A1 | 3/2018 | De Graff et al. |
| 2018/0078305 A1 | 3/2018 | Rioux et al. |
| 2018/0104004 A1 | 4/2018 | Rioux et al. |
| 2018/0132833 A1 | 5/2018 | Gotlib |
| 2018/0153637 A1 | 6/2018 | Al-Shawi et al. |
| 2019/0314084 A1 | 10/2019 | Rioux |
| 2021/0275244 A1 | 9/2021 | Rioux et al. |

(56) References Cited

U.S. PATENT DOCUMENTS

FOREIGN PATENT DOCUMENTS

| DE | 102010032932 A1 | 2/2012 |
|---|---|---|
| EP | 0777445 B1 | 6/1999 |
| EP | 2942023 A3 | 2/2016 |
| EP | 3040043 B1 | 1/2018 |
| JP | 3009735 B2 | 2/2000 |
| JP | 2010-505596 | 2/2010 |
| JP | 2010-505596 A | 2/2010 |
| JP | 2010-155083 | 7/2010 |
| JP | 2010-155083 A | 7/2010 |
| JP | 2013-532552 | 8/2013 |
| JP | 2013-532552 A | 8/2013 |
| JP | 2015-100706 | 6/2015 |
| JP | 2015-100706 A | 6/2015 |
| JP | 2016-127919 | 7/2016 |
| JP | 2016-127919 A | 7/2016 |
| WO | 9510326 A1 | 4/1995 |
| WO | 9942047 A1 | 8/1999 |
| WO | 0051683 A1 | 9/2000 |
| WO | 01/74252 | 10/2001 |
| WO | 01/74252 A2 | 10/2001 |
| WO | 2007/103986 A2 | 9/2007 |
| WO | 2011/143468 A2 | 11/2011 |
| WO | 2012/015722 A1 | 2/2012 |
| WO | 2012/050637 A1 | 4/2012 |
| WO | 2013134733 A3 | 11/2013 |
| WO | 2014/022379 A1 | 2/2014 |
| WO | 2014/189887 A2 | 11/2014 |
| WO | 2015/142674 A1 | 9/2015 |
| WO | 2015/163846 A1 | 10/2015 |
| WO | 2015/200518 A1 | 12/2015 |
| WO | 2016/176567 | 11/2016 |
| WO | 2016/176567 A1 | 11/2016 |
| WO | 2016/181316 | 11/2016 |
| WO | 2016/181316 A1 | 11/2016 |
| WO | 2016/181318 A1 | 11/2016 |
| WO | 2019023328 A1 | 1/2019 |

OTHER PUBLICATIONS

Non-Final Office Action issued in U.S. Appl. No. 16/633,934, dated Jul. 25, 2022, 19 pages.
Non-Final Office Action issued in U.S. Appl. No. 16/001,494, dated Nov. 26, 2021, 18 pages.
International Search Report and Written Opinion issued in International Application No. PCT/US2022/041881, dated Dec. 13, 2022, 26 pages.
Extended European Search Report issued European Patent Application No. 18839274.0, dated Mar. 15, 2021 (9 pages).
Extended European Search Report issued in European Patent Application No. 18839345.8, dated Mar. 12, 2021 (9 pages).
International Search Report and Written Opinion issued in International Application No. PCT/US2018/043658, dated Nov. 15, 2018 (13 pages).
International Search Report and Written Opinion issued in International Application No. PCT/US2020/033357, dated Aug. 27, 2020 (5 pages).
ISA—Search Strategy—Issued by the Israel Patent Office for International Application No. PCT/US2018/043658, dated Nov. 14, 2018 (1 page).
"Aquamantys System" Product Brochure, Medtronic, 2014 (12 Pages).
"Starburst Talon" Specifications Brochure, Angiodynamics, 2013 (2 Pages).
Chinese Office Action and English summary issued in Chinese Application No. 201680062908.2, dated Jun. 30, 2020, 12 pages.
Extended European Search Report issued in European Application No. 13825361.2, dated Jun. 10, 2016, 12 pages.
Extended European Search Report issued in European Application No. 16787228.2, dated Nov. 27, 2018, 6 pages.
Extended European Search Report issued in European Application No. 16860886.7, dated Jun. 12, 2019, 8 pages.
Extended European Search Report issued in European Application No. 17747970.6, dated Jul. 16, 2019, 6 pages.
Extended European Search Report issued in European Application No. 17828289.3, dated Feb. 6, 2020, 5 pages.
Extended European Search Report issued in European Application No. 17895158.8, dated Feb. 28, 2020, 8 pages.
Extended European Search Report issued in European Application No. 18757994.1, dated Nov. 24, 2020, 8 pages.
Extended European Search Report issued in European Application No. 19219030.4, dated Jun. 26, 2020, 6 pages.
Extended European Search Report issued in European Patent Application No. 18812643.7, dated Feb. 9, 2021, 7 pages.
International Search Report and Written Opinion of the Interational Searching Authority dated Feb. 27, 2018 for International Application No. PCT/US2017/056754 (11 Pages).
International Search Report and Written Opinion of the International Searching Authority dated Aug. 22, 2016 for International Application No. PCT/US2016/030081 (11 Pages).
International Search Report and Written Opinion of the International Searching Authority dated Aug. 26, 2018 for International Application No. PCT/US2017/059850 (10 Pages).
International Search Report and Written Opinion of the International Searching Authority dated Aug. 5, 2015 for International Application No. PCT/US2015/020596 (13 Pages).
International Search Report and Written Opinion of the International Searching Authority dated Feb. 2, 2017 for International Application No. PCT/US2016/059345 (10 Pages).
International Search Report and Written Opinion of the International Searching Authority dated Jun. 11, 2017 for International Application No. PCT/US2017/019398 (27 Pages).
International Search Report and Written Opinion of the International Searching Authority dated May 16, 2017 for International Application No. PCT/US2017/015582 (11 pages).
International Search Report and Written Opinion of the International Searching Authority dated May 16, 2017 for International Application No. PCT/US2017/015584 (11 pages).
International Search Report and Written Opinion of the International Searching Authority dated Nov. 1, 2018 for International Application No. PCT/US2018/043654 (10 Pages).
International Search Report and Written Opinion of the International Searching Authority dated Nov. 15, 2018 for International Application PCT/US2018/043658 (15 Pages).
International Search Report and Written Opinion of the International Searching Authority dated Nov. 29, 2013 for International Application No. PCT/US2013/052703 (11 Pages).
International Search Report and Written Opinion of the International Searching Authority dated Oct. 19, 2017 for International Application No. PCT/US2017/041501 (63 Pages).
International Search Report and Written Opinion of the International Searching Authority dated Sep. 16, 2018 for International Application No. PCT/US2018/036268 (11 Pages).
International Search Report and Written Opinion of the International Searchng Authority dated Jun. 6, 2018 for International Application No. PCT/US2018/019151 (17 Pages).
Japanese Office Action and English translation issued in Japanese Application No. 2018-521973, dated Nov. 4, 2020, 8 pages.
Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).
Non-Final Office Action dated Aug. 11, 2017 for U.S. Appl. No. 15/337,334 (11 Pages).
Non-Final Office Action dated Aug. 11, 2017 for U.S. Appl. No. 15/624,327 (11 Pages).
Non-Final Office Action dated Aug. 4, 2017 for U.S. Appl. No. 15/624,230 (18 Pages).
Non-Final Office Action dated May 7, 2018 for U.S. Appl. No. 15/142,616 (13 Pages).
Notice of Allowance dated Jul. 24, 2018 for U.S. Appl. No. 15/784,778 (12 Pages).

(56) References Cited

OTHER PUBLICATIONS

Official Action issued in Japanese Patent Application No. 2018-540040, dated Jun. 19, 2019, 11 pages.
Response to Non-Final Office Action Filed Sep. 19, 2017 for U.S. Appl. No. 15/624,327 (8 Pages).
Response to Non-Final Office Action Filed Sep. 20, 2017 for U.S. Appl. No. 15/337,334 (6 Pages).
Response to Non-Final Office Action Filed Sep. 20, 2017 for U.S. Appl. No. 15/624,230 (10 Pages).
International Search Report and Written Opinion issued in International Application No. PCT/US2022/011296, dated Mar. 25, 2022, 9 pages.
Non-Final Office Action issued in U.S. Appl. No. 16/876,284, dated Apr. 19, 2022, 13 pages.
International Search Report and Written Opinion of the International Searching Authority dated Aug. 27, 2020 for International Application No. PCT/US2020/033355 (4 pages).
International Search Report and Written Opinion of the International Searching Authority dated Aug. 27, 2020 for International Application No. PCT/US2020/033355 (5 pages).
Office Action issued in U.S. Appl. No. 16/633,765, dated Nov. 5, 2021, 9 pages.
European Office Action issued in European Application No. 18839345.8, dated May 23, 2022, 4 pages.

\* cited by examiner

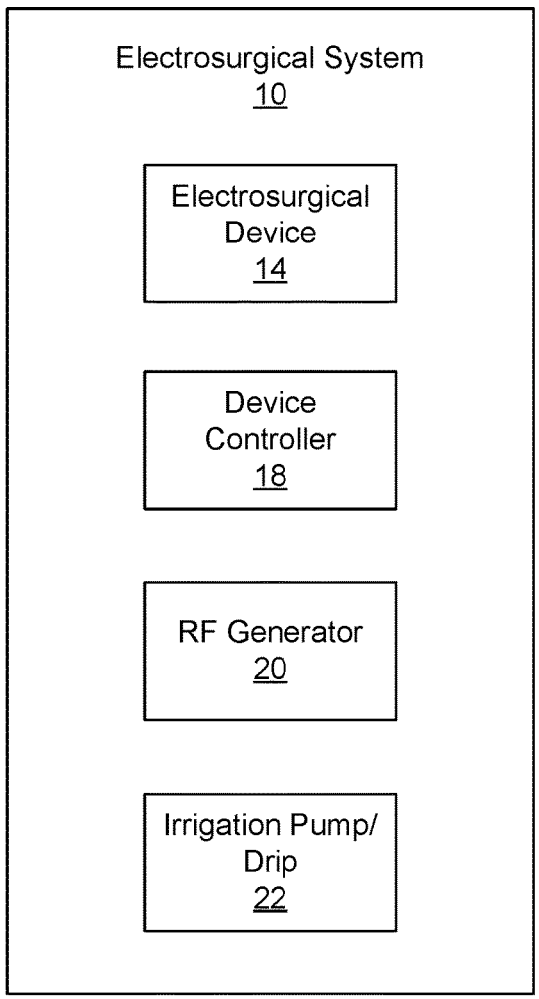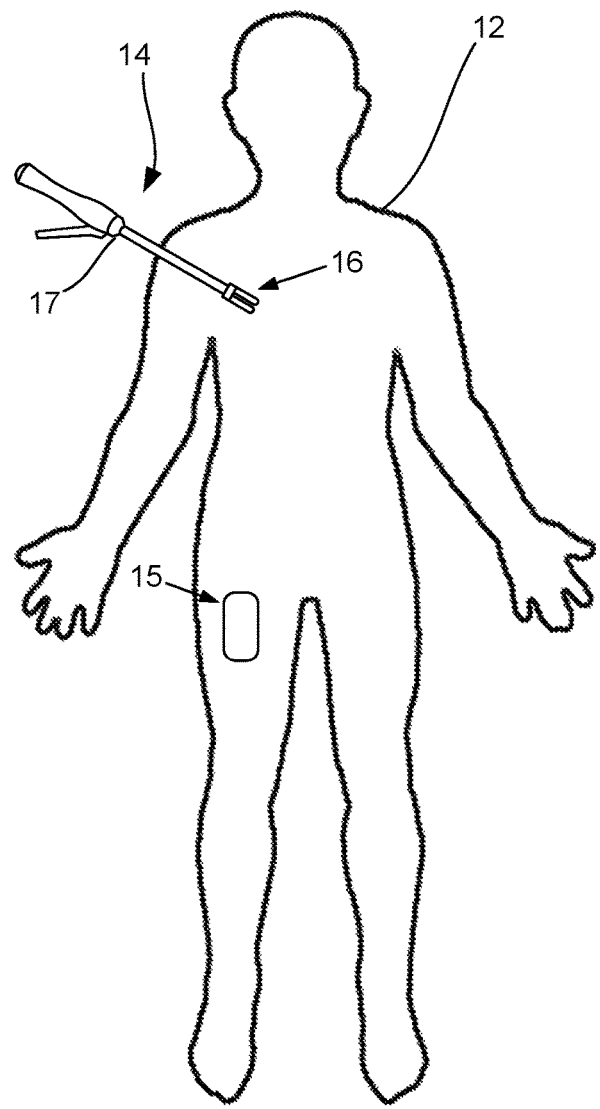
FIG. 1A
FIG. 1B

ELECTROSURGICAL TISSUE AND VESSEL SEALING DEVICE

CROSS-REFERENCE TO RELATED APPLICATIONS

This application is a continuation of U.S. Ser. No. 15/802,760, filed Nov. 3, 2017, now U.S. Pat. No. 10,912,602, which claims the benefit of, and priority to, U.S. Provisional Application No. 62/419,227, filed Nov. 8, 2016, the content of which is hereby incorporated by reference herein in its entirety.

FIELD

The present disclosure relates generally to medical devices for sealing tissue, and, more particularly, to an electrosurgical device in the form of forceps including an end effector assembly including opposing jaws for providing controlled compression and energy emission for sealing, cauterizing, coagulating, and/or desiccating vessels and vascular tissue including been previously sutured or stapled.

BACKGROUND

Most surgical procedures require some form of closure of a vessel, wound, or incision. For example, in many procedures, a surgeon will rely on sutures as a means of surgically occluding a vessel, closing wounds, as well as coupling portions of tissue to one another (e.g., bypass surgeries and anastomoses formation). More recently, surgical staples and clips have become commonly used in place of sutures, where appropriate, as stapling can be much faster than suturing by hand, and can also be more accurate and consistent. Furthermore, stapling may not require the degree of experience and expertise that suturing generally requires. Staples may primarily be used in bowel and lung surgery, because staple lines may be more consistent and therefore less likely to leak blood, air or bowel contents.

While the use of staples for thoracic surgery has been widely accepted and regarded as a safe procedure, there are instances in which stapling is may be insufficient and unable to achieve complete closure of a wound, incision, or vessel. This may be particularly critical in certain thoracic procedures, particularly those involving pulmonary vasculature where the leakage of air and/or fluid contents can be life threatening.

In some procedures, a surgeon may rely on an electrosurgical device to seal or cauterize a vessel, wound, or incision by applying energy (e.g., electrical current, radiofrequency (RF), thermal energy, etc.) to the target tissue or vessel. Some current devices, particularly electrosurgical forceps, use mechanical action between opposing jaws to constrict tissue and further apply electrical energy to effect hemostasis by heating the tissue and blood vessels to coagulate, cauterize, cut and/or seal tissue. While current electrosurgical forceps allow for the sealing of tissue or vessels, such devices have shortcomings and are unable to be used in conjunction with sutures and/or staples. For example, some sutures and staples may be fragile (e.g., formed from bioabsorbable materials) and thus may be unable to withstand the compression forces and/or energy delivered via current electrosurgical forceps. Thus, the use of current electrosurgical forceps on a vessel or wound that includes a suture or staple may result in damage to the suture or staple, which may compromise the integrity of the seal and may further result in serious complications, such as an increase in wound severity as well as life-threating infection.

SUMMARY

An electrosurgical device can be delivered to a surgical site to provide sealing of vessels and/or vascular tissue. The device is useful for supplementing an initial closure of a vessel, wound, or incision via suturing or stapling. In particular, the device is configured to apply controlled compression and energy emission to the vessel, wound, or incision while maintaining the integrity of the suture or staple (i.e., without damaging the suture or staple). Accordingly, the electrosurgical device of the present disclosure provides for complete closure, thereby preventing leakage of air, contents, or fluid and subsequently preventing infection or life threatening complications.

The electrosurgical device is generally in the form of forceps and includes a probe acting as a handle and an end effector assembly positioned at a distal end of the probe. The end effector assembly includes opposing jaws configured to move relative to one another between open and closed positions upon corresponding input from the surgeon (i.e., via control from a trigger on the probe). Each jaw includes a deformable pad or cushion including an electrode array positioned along an exterior surface thereof and is configured to provide controlled compression upon a target tissue or vessel and subsequent delivery of radiofrequency (RF) energy for effectively sealing, cauterizing, coagulating, and/or desiccating the target tissue or vessel while maintaining the integrity of any suture(s) or staple(s).

In particular, the deformable cushion may generally include a nonconductive material that is flexible and configured to transition from a default shape (e.g., generally planar contact surface) to a deformed shape (e.g., one or more portions of contact surface become compressed) upon contact with a vessel or tissue and corresponding suture(s) or staple(s). The compression of the cushion allows for the electrode array to better conform to the contour of the target tissue or vessel on either side of a suture or staple, thereby improving contact and ablation/coagulation performance and enabling effective sealing around the suture or staple.

The electrode array on each cushion is configured to emit a non-ionizing radiation, such as RF energy, in a bipolar configuration for sealing, cauterizing, coagulating, and/or desiccating the vessel or tissue. The electrode array is composed of one or more conductive members (e.g., conductive wires) positioned along a length of the exterior surface of the cushion. In some embodiments, each of the plurality of conductive wires, or one or more sets of a combination of conductive wires, may be configured to independently receive an electrical current from an energy source (e.g., RF generator) and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wires) can function as a ground or neutral conductive member.

The electrosurgical device is configured to deliver the RF energy via a virtual electrode arrangement, which includes distribution of a fluid along the exterior surface of each cushion and, upon activation of the electrode array, the fluid may carry, or otherwise promote, energy emitted from the electrode array to the surrounding tissue. In particular, each cushion includes one or more perforations in fluid communication with at least one lumen of the probe shaft configured receive a fluid, such as saline, from a fluid source. The one or more perforations allow the passage of the fluid to the exterior surface of the cushion. Upon transitioning the opposing jaws to the closed position, the corresponding cushions engage opposing sides of the target tissue or vessel, including one or more sutures or staples. The surgeon can apply force so as to compress the target tissue or vessel between the opposing cushions, wherein the exterior surface of each cushion generally conforms to the surface of the tissue or vessel and the suture(s) or staple(s) while maintaining the integrity of the suture or staple (i.e., without damaging the suture or staple). Due to the conforming nature of the cushions, each electrode array is able to come into contact with, and effectively seal, portions of the target tissue or vessel that are immediately adjacent to the suture(s) or staple(s), which are generally missed with current electrosurgical forceps.

The surgeon may then activate both the fluid delivery and electrode array, each of which can be independently controlled via a controller. The fluid weeping through the perforations to the outer surface of the cushions is able to carry energy from electrode array, thereby creating a virtual electrode. Upon the fluid weeping through the perforations, a pool or thin film of fluid is formed on the exterior surface of the cushions and is configured to seal portions of the target tissue of vessel in contact therewith via the RF energy carried from the electrode array. Accordingly, the electrosurgical device of the present disclosure provides for complete closure of the target tissue or vessel, thereby preventing or reducing the risk of leakage of air, contents, or fluid and subsequently preventing infection or life threatening complications that may otherwise occur with simply a suture or staple closure.

The electrosurgical device of the present disclosure provides numerous advantages. In particular, the electrosurgical device is useful for supplementing an initial closure of a vessel, wound, or incision via suturing or stapling. The deformable cushion on each opposing jaw is configured to deform upon being compressed against the target tissue or vessel and the suture(s) or staple(s) such that the exterior surface of each cushion conforms and corresponds to the tissue or vessel surface and suture(s) or staple(s). The cushion is able to be compressed against the suture or staple without causing physical damage thereto or compromising the structural integrity of the suture or staple. Furthermore, due to the conforming nature of the cushions, each electrode array is able to come into contact with, and effectively seal, portions of the target tissue or vessel that are immediately adjacent to the suture(s) or staple(s), which are generally missed with current electrosurgical forceps as a result of the rigid, non-compliant sealing plates of such forceps. The virtual electrode arrangement of the present device further allows for a non-sticking surface during a sealing procedure, as the saline generally acts as a buffer between the tissue surface and the surface of the conductive wires. Furthermore, the virtual electrode provides for controlled emission of energy, including at least length of elapsed time and intensity, which, in turn, effectively controls the thermal energy released for sealing, which can be consistently maintained between 60° C. and 100° C. to prevent inadvertent damage to surrounding tissue.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIGS. 1A and 1B are schematic illustrations of an electrosurgical system consistent with the present disclosure;

Figure 2:
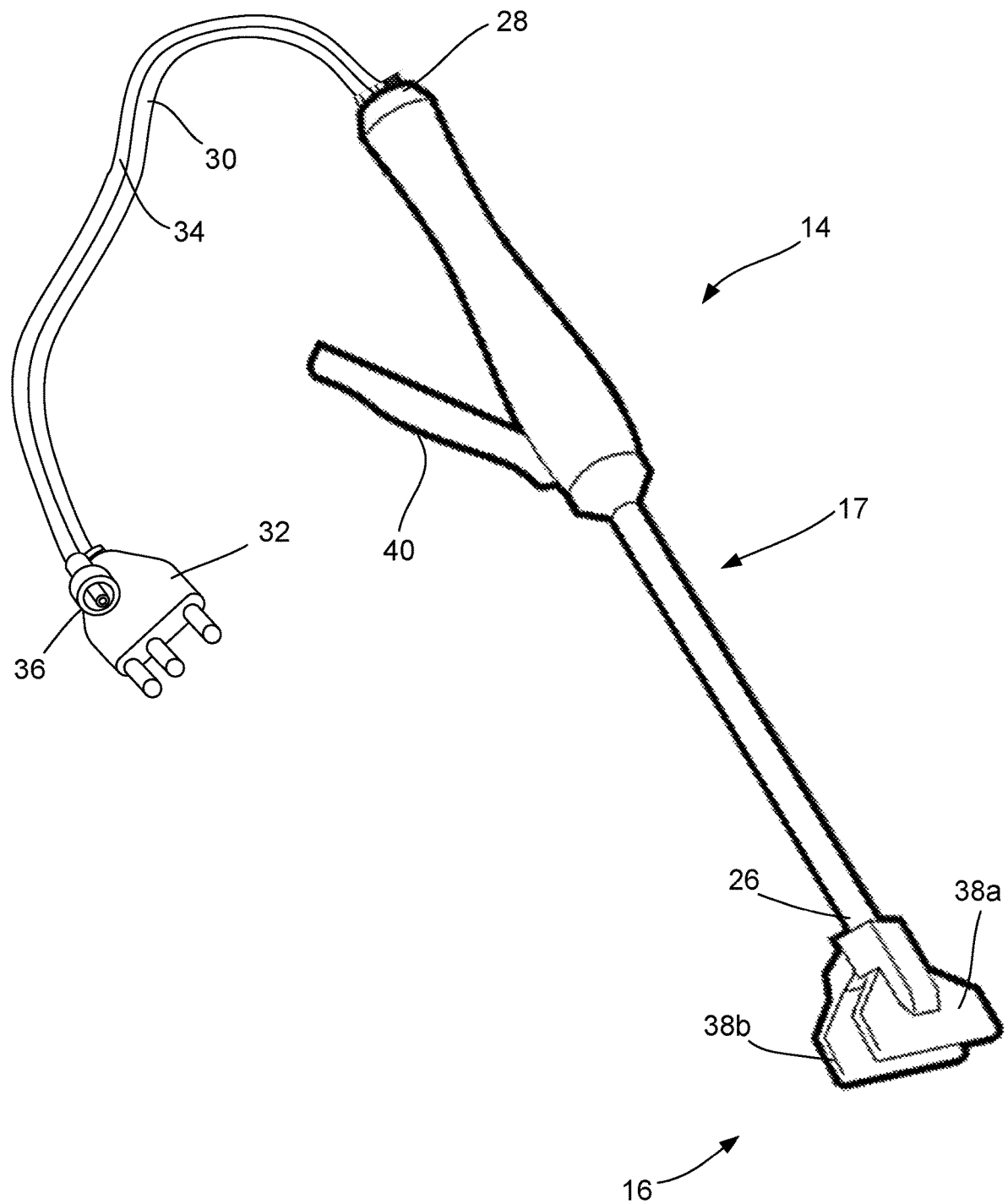
FIG. 2 is a perspective view of one embodiment of an electrosurgical device compatible with the system of FIG. 1A.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to an electrosurgical device can be delivered to a surgical site to provide sealing of vessels and/or vascular tissue. The device is useful for supplementing an initial closure of a vessel, wound, or incision via suturing or stapling. In particular, the device is configured to apply controlled compression and energy emission to the vessel, wound, or incision while maintaining the integrity of the suture or staple (i.e., without damaging the suture or staple). Accordingly, the electrosurgical device of the present disclosure provides for complete closure, thereby preventing leakage of air, contents, or fluid and subsequently preventing infection or life threatening complications.

The electrosurgical device is generally in the form of forceps and includes a probe acting as a handle and an end effector assembly positioned at a distal end of the probe. The end effector assembly includes opposing jaws configured to move relative to one another between open and closed positions upon corresponding input from the surgeon (i.e., via control from a trigger on the probe). Each jaw includes a deformable pad or cushion including an electrode array positioned along an exterior surface thereof and is configured to provide controlled compression upon a target tissue or vessel and subsequent delivery of radiofrequency (RF) energy for effectively sealing, cauterizing, coagulating, and/or desiccating the target tissue or vessel while maintaining the integrity of any suture(s) or staple(s). The electrosurgical device is configured to deliver radiofrequency (RF) energy via a virtual electrode arrangement, which includes distribution of a fluid along the exterior surface of each cushion and, upon activation of the electrode array, the fluid may carry, or otherwise promote, energy emitted from the electrode array to the surrounding tissue. In particular, each cushion includes one or more perforations in fluid communication with at least one lumen of the probe shaft configured receive a fluid, such as saline, from a fluid source. The one or more perforations allow the passage of the fluid to the exterior surface of the cushion. Upon transitioning the opposing jaws to the closed position, the corresponding cushions engage opposing sides of the target tissue or vessel, including one or more sutures or staples. The surgeon can apply force so as to compress the target tissue or vessel between the opposing cushions, wherein the exterior surface of each cushion generally conforms to the surface of the tissue or vessel and the suture(s) or staple(s) while maintaining the integrity of the suture or staple (i.e., without damaging the suture or staple). Due to the conforming nature of the cushions, each electrode array is able to come into contact with, and effectively seal, portions of the target tissue or vessel that are immediately adjacent to the suture(s) or staple(s), which are generally missed with current electrosurgical forceps.

The surgeon may then activate both the fluid delivery and electrode array, each of which can be independently controlled via a controller. The fluid weeping through the perforations to the outer surface of the cushions is able to carry energy from electrode array, thereby creating a virtual electrode. Upon the fluid weeping through the perforations, a pool or thin film of fluid is formed on the exterior surface of the cushions and is configured to seal portions of the target tissue or vessel in contact therewith via the RF energy carried from the electrode array. Accordingly, the electrosurgical device of the present disclosure provides for complete closure of the target tissue or vessel, thereby preventing or reducing the risk of leakage of air, contents, or fluid and subsequently preventing infection or life threatening complications that may otherwise occur with simply a suture or staple closure.

FIGS. 1A and 1B are schematic illustrations of an electrosurgical system 10 for providing sealing of vessels and/or tissue of a patient 12. The electrosurgical system 10 generally includes an electrosurgical device 14, which includes a probe including an end effector assembly 16 and an elongated catheter shaft 17 to which the end effector assembly 16 is coupled. The catheter shaft 17 may generally include a nonconductive elongated member including at least a fluid delivery lumen, as will be described in greater detail herein. The electrosurgical device 14 may further be coupled to a device controller 18, a radiofrequency (RF) generator 20 over an electrical connection (electrical line 30 shown in FIG. 2), and an irrigation pump or drip 22 over a fluid connection (fluid line 34 shown in FIG. 2).

The device controller 18 may include hardware/software configured to provide a user with the ability to control electrical output to the electrosurgical device 14 in a manner so as to control energy output to a tissue or vessel intended to be sealed or that has initially undergone suturing or stapling. For example, as will be described in greater detail herein, the electrosurgical device may be configured to operate at least in a "bipolar mode" based on input from a user (e.g., surgeon, clinician, etc.) resulting in the emission of radiofrequency (RF) energy in a bipolar configuration. In some embodiments, the device 14 may be configured to operate in other modes, such as a "measurement mode", in which data can be collected, such ascertain measurements (e.g., temperature, conductivity (impedance), etc.) that can be taken and further used by the controller 18 so as to provide an estimation of the state of tissue during a sealing procedure, as will be described in greater detail herein. In some embodiments, the device controller 18 may be housed within the electrosurgical device 14. The RF generator 20 may also be connected to a separate return electrode 15 that is attached to the skin of the patient 12.

As will be described in greater detail herein, during a sealing procedure, the generator 20 may generally provide RF energy (e.g., electrical energy in the radiofrequency (RF) range (e.g., 350-800 kHz)) to an electrode array of the electrosurgical device 14, as controlled by the device controller 18. At the same time, saline may also be provided to and released from the end effector assembly 16. In some embodiments, the RF energy travels through the blood and tissue of the patient 12 to a return electrode and, in the process, provides energy emission (e.g., sealing, cauterizing, coagulating and/or desiccating) to tissue adjacent to portions of the electrode array that have been activated.

FIG. 2 is a perspective view of electrosurgical device 14. As previously described, the electrosurgical device 14 includes a probe 17 including an elongated shaft configured as a handle and adapted for manual manipulation. Accordingly, as shown in FIG. 2, the probe 17 is in the form of a handle including a distal end 26 to which the end effector assembly 16 is coupled and a proximal end 28. The probe 17 may generally resemble forceps, for example, and thus may further include a trigger 40 allowing for a surgeon to control operation of the end effector assembly 16 (i.e., control opening and closing of opposing jaws 38a, 38b), as will be described in greater detail herein. As shown, the proximal end 28 of the probe 17 may be coupled to the generator 20 and the irrigation pump 22 via connection lines or fittings. For example, the probe 17 is coupled to the generator 20 via an electrical line 30 and coupled to the irrigation pump 22 via a fluid line 34. Each of the electrical line 30 and fluid line 34 may include an adaptor end 32 and 36 configured to couple the associated lines with a respective interface on the generator 20 and irrigation pump 22.

In some examples, the electrosurgical device 14 may further include a user interface (not shown) serving as the device controller 18 and in electrical communication with at least one of the generator 20, the irrigation pump 22, and the electrosurgical device 14. The user interface may include, for example, selectable buttons for providing an operator with one or more operating modes with respect to controlling the energy emission output of the device 14, as will be described in greater detail herein. For example, selectable buttons may allow a user to control electrical output to the electrosurgical device 14 in a manner so as to control the sealing, cauterizing, coagulating, and/or desiccating of portions of a tissue or vessel. Furthermore, in some embodiments, selectable buttons may provide an operator to control the delivery of fluid from the irrigation pump 22. As shown, the end effector assembly 16 includes first and second jaws 38a, 38b generally opposing one another and configured to move relative to one another in response to user interaction with the trigger 40, as will be described in greater detail herein.

Figure 3:
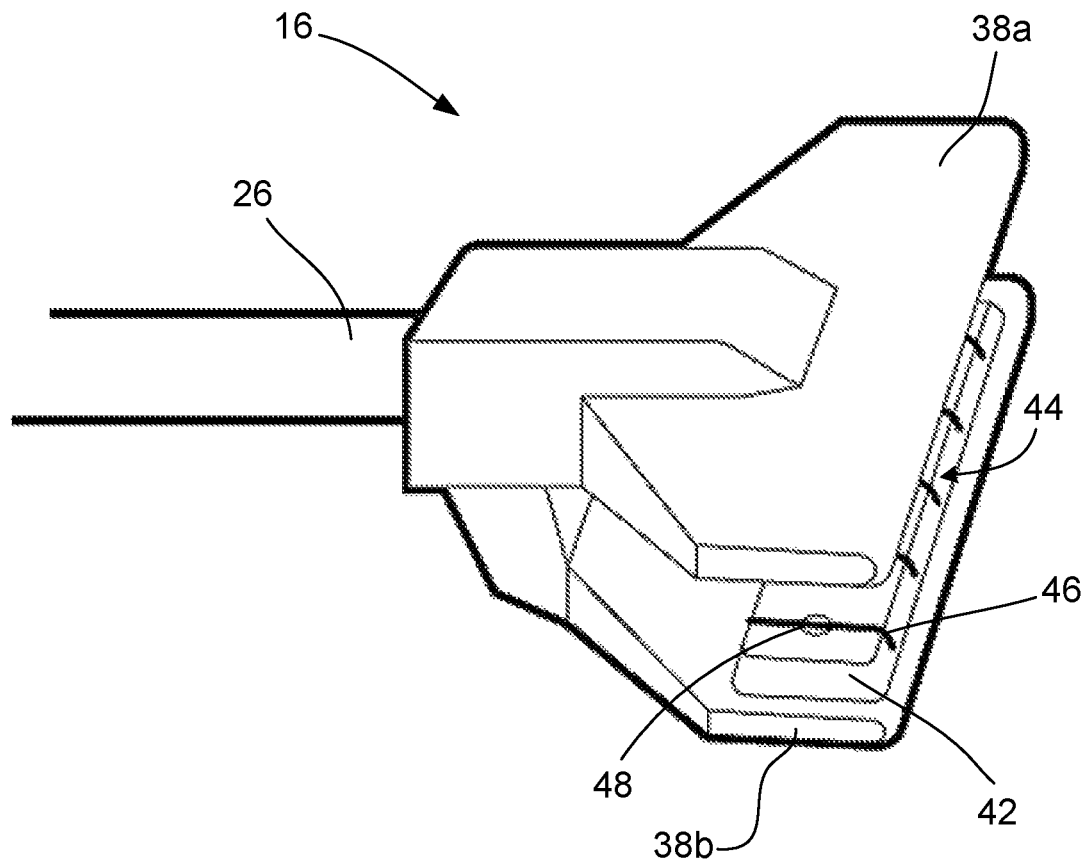
FIG. 3 is an enlarged view of the end effector assembly of the device of FIG. 2 in greater detail.

FIG. 3 is an enlarged view of the end effector assembly 16 in greater detail. As shown, each jaw 38a, 38b includes a deformable pad or cushion (hereinafter referred to as "cushion 42") including an electrode array 44 positioned along an exterior surface thereof. Each cushion 42 is configured to provide controlled compression upon a target tissue or vessel and subsequent delivery of radiofrequency (RF) energy for effectively sealing, cauterizing, coagulating, and/or desiccating the target tissue or vessel while maintaining the integrity of any sutures or staples on the target tissue or vessel.

In particular, the deformable cushion may generally include a nonconductive material that is flexible and configured to transition from a default shape (e.g., generally planar contact surface) to a deformed shape (e.g., one or more portions of contact surface become compressed) upon contact with a vessel or tissue and corresponding sutures or staples (see FIGS. 9A and 9B). Accordingly, the nonconductive deformable cushion 42 may include an elastomeric or shape memory material. The compression of the cushion 42 allows for the electrode array 44 to better conform to the contour of the target tissue or vessel on either side of a suture or staple, thereby improving contact and ablation/coagulation performance and enabling effective sealing around the suture or staple.

Figure 4:
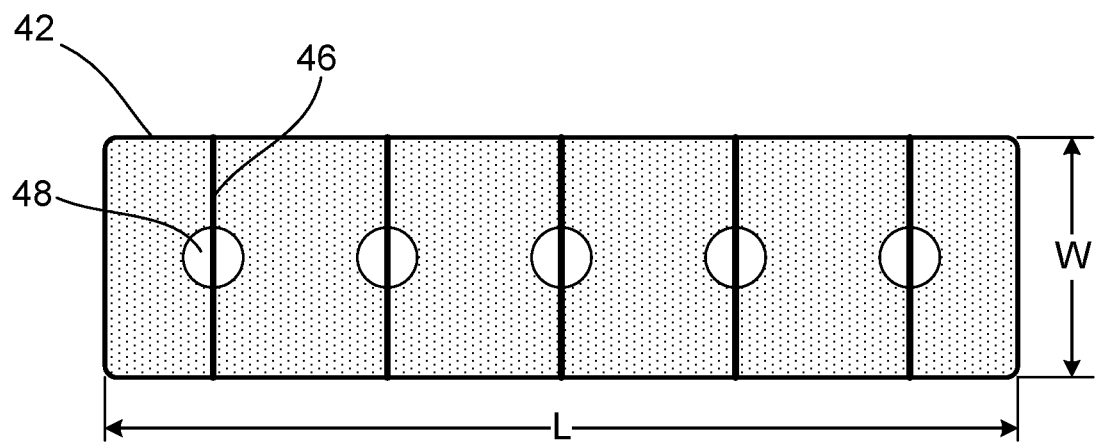
FIG. 4 is a plan view of an exterior contact surface of a deformable cushion and an electrode array positioned thereon.

FIG. 4 is a plan view of an exterior contact surface of a deformable cushion 42 and an electrode array 44 positioned thereon. The cushion 42 may have a length L in the range of 2-10 cm, and, in some embodiments, the length L may be 3-5 cm. The cushion 42 may have a width in the range of 0.5 mm to 3 mm, and, in some instances, is in the range of 0.7 to 1 mm. The electrode array 44 on each cushion 42 is configured to emit a non-ionizing radiation, such as RF energy, in a bipolar configuration for sealing, cauterizing, coagulating, and/or desiccating the vessel or tissue. The electrode array 44 is composed of one or more conductive members 46 (e.g., hereinafter referred to as "conductive wire(s) 46") positioned along a length of the exterior surface of the cushion 42. In some embodiments, each of the plurality of conductive wires 46, or one or more sets of a combination of conductive wires 46, may be configured to independently receive an electrical current from an energy source (e.g., the RF generator 20) and independently conduct energy, the energy including RF energy. This allows energy to be selectively delivered to a designated conductive wire 46 or combination of conductive wires 46. This design also enables the electrosurgical device 14 to function in a bipolar mode because a first conductive wire (or combination of conductive wires) can deliver energy to the surrounding tissue through its electrical connection with an RF generator while a second conductive wire (or combination of conductive wires) can function as aground or neutral conductive member. The conductive wires 46 can be formed of any suitable conductive material (e.g., a metal such as stainless steel, nitinol, or aluminum).

Since each conductive wire 46 in the electrode array 44 may be electrically independent, each conductive wire 46 can be connected in a fashion that allows for impedance measurements using bipolar impedance measurement circuits. For example, the conductive wires can be configured in such a fashion that tetrapolar or guarded tetrapolar electrode configurations can be used. For instance, one pair of conductive wires could function as the current driver and the current return, while another pair of conductive wires could function as a voltage measurement pair. Accordingly, a dispersive ground pad can function as current return and voltage references.

The electrosurgical device 14 is configured to deliver the RF energy via a virtual electrode arrangement, which includes distribution of a fluid along the exterior surface of each cushion 42 and, upon activation of the electrode array 44, the fluid may carry, or otherwise promote, energy emitted from the electrode array 44 to the surrounding tissue. In particular, each cushion 42 includes one or more perforations 48 in fluid communication with at least one lumen of the probe shaft configured receive a fluid, such as saline, from a fluid source (e.g., the irrigation drip 22). The one or more perforations 48 allow the passage of the fluid to the exterior surface of the cushion 42. As shown, each of the perforations 48 are generally aligned with an associated conductive wire 46. Accordingly, upon fluid weeping through the perforations 48, a pool or thin film of fluid is formed on the exterior surface of the cushion 42 and configured to ablate and/or coagulate via the electrical current conducted by the one or more conductive wires 46 of the electrode array 44, as described in greater detail herein.

Figure 5A:
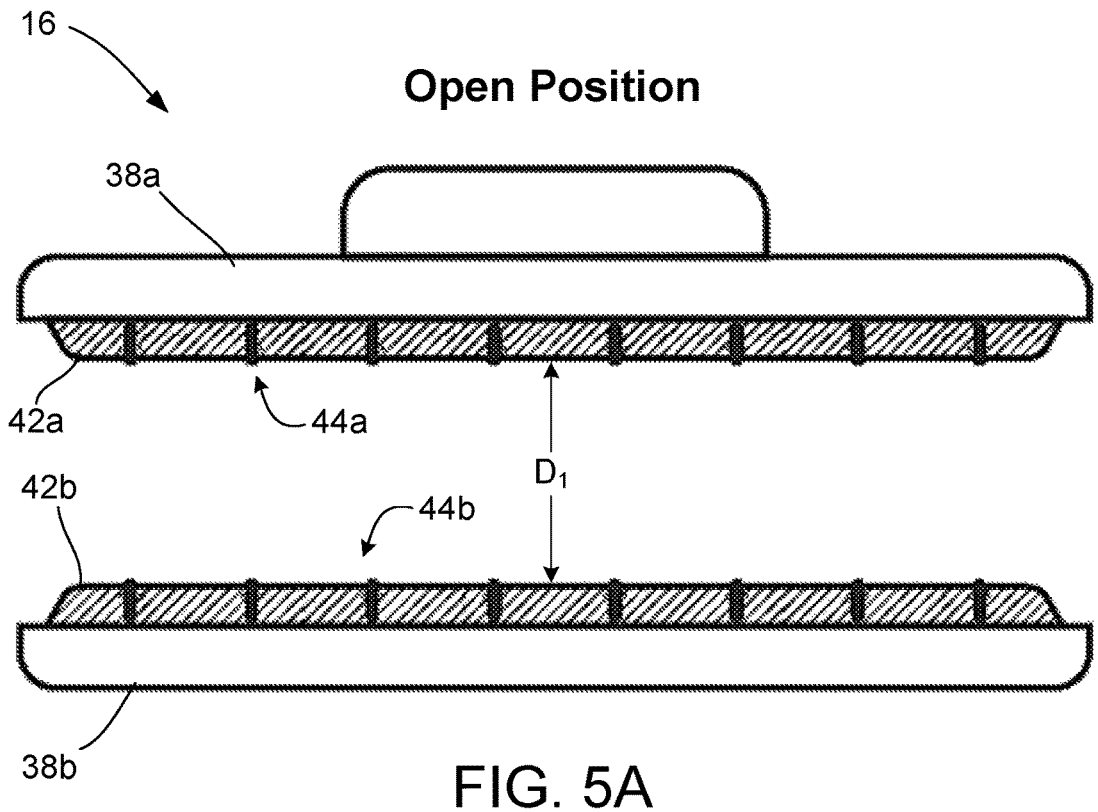
FIGS. 5A and 5B are front views of the opposing jaws of the end effector assembly of the device of FIG. 2 in open and closed positions, respectively.
Figure 5B:
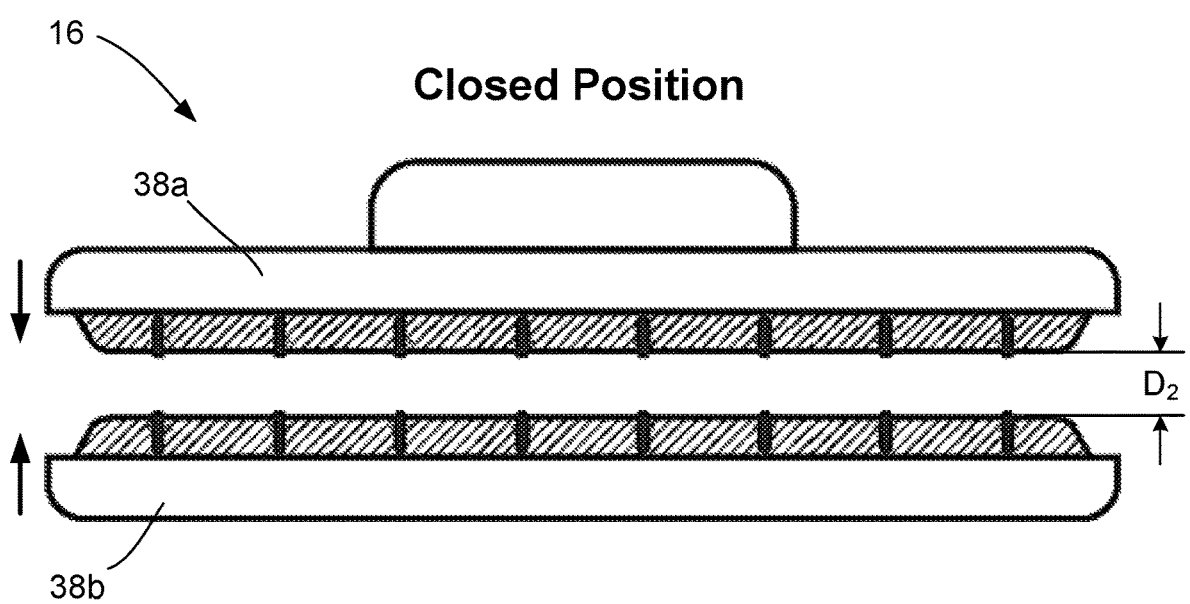

FIGS. 5A and 5B are front views of the opposing jaws 38a, 38b of the end effector assembly 16 in open and closed positions, respectively. In some embodiments, both jaws 38a, 38b may move relative to one another and the probe shaft. In other embodiments, one of the jaws 38 may be fixed in position relative to the probe shaft while the other jaw 38 is configured to move relative to both the fixed jaw and the probe shaft. The opposing jaws 38a, 38b are configured to transition between open and closed positions in response to user input with the trigger 40, as shown in FIGS. 5A and 5B. For example, in the default open position, both jaws are spaced a distance $D_1$ apart when the trigger 40 is not compressed. The distance $D_1$ between the jaws 38a, 38b may generally be sufficient to receive a stapled portion of tissue or vessel there between. Once the target portion of tissue or vessel is positioned between the opposing jaws 38a, 38b when in the open position, the surgeon need only compress the trigger 40, which, in turn, results in movement of the jaws 38a, 38b towards one another and the target portion of tissue or vessel be held or grasped in between the jaws 38a, 38b as the distance there between decreases until at least a distance $D_2$ is reached, in which the target portion of tissue or vessel is compressed between the jaws 38a, 38b. Upon transitioning the jaws 38a, 38b to the closed position, sealing, cauterizing, coagulating, and/or desiccating of the target portion of tissue or vessel can occur, as will be described in greater detail herein.

Figure 6:
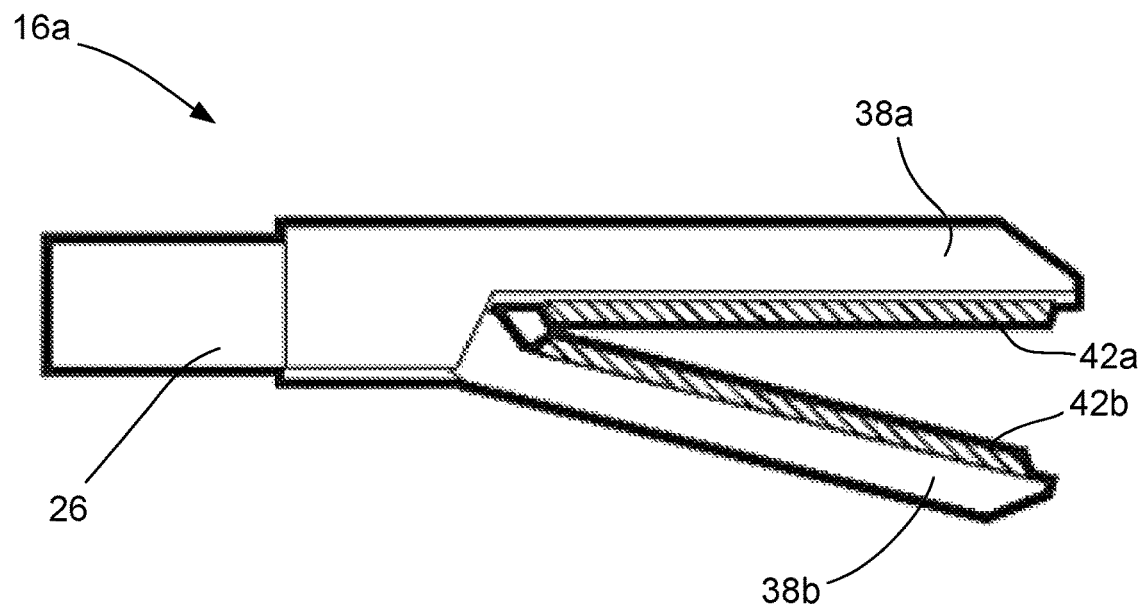
FIG. 6 is an enlarged view of another embodiment of an end effector assembly compatible with an electrosurgical device consistent with the present disclosure.
Figure 7:
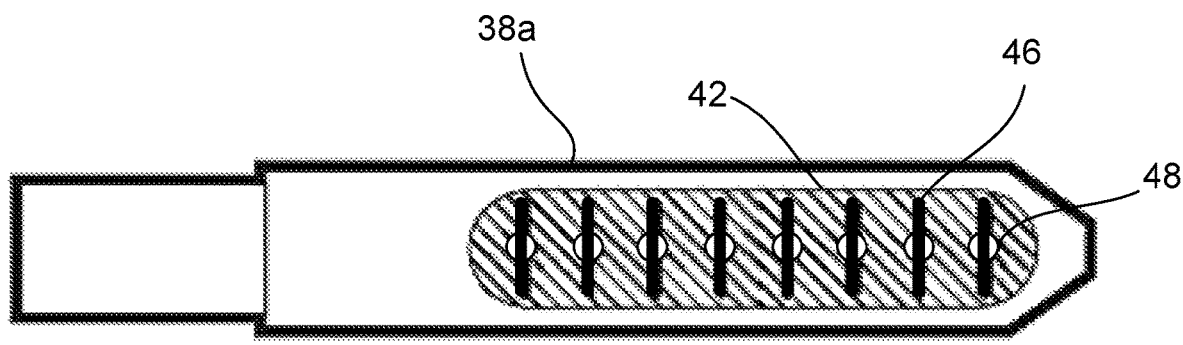
FIG. 7 is a plan view of one of the opposing jaws of the end effector assembly of FIG. 6 illustrating the deformable cushion and electrode array provided thereon.

FIG. 6 is an enlarged view of another embodiment of an end effector assembly 16a compatible with an electrosurgical device 14 consistent with the present disclosure. Unlike the end effector assembly 16 of FIGS. 2, 3, 4, and 5A-5B, the end effector assembly 16a is configured to laparoscopic procedures, in that the opposing jaws 38a, 38b include atraumatic tips and have a much more narrow profile. FIG. 7 is a plan view of one of the opposing jaws 38a of the end effector assembly 16a illustrating the deformable cushion and electrode array provided thereon.

Figure 8:
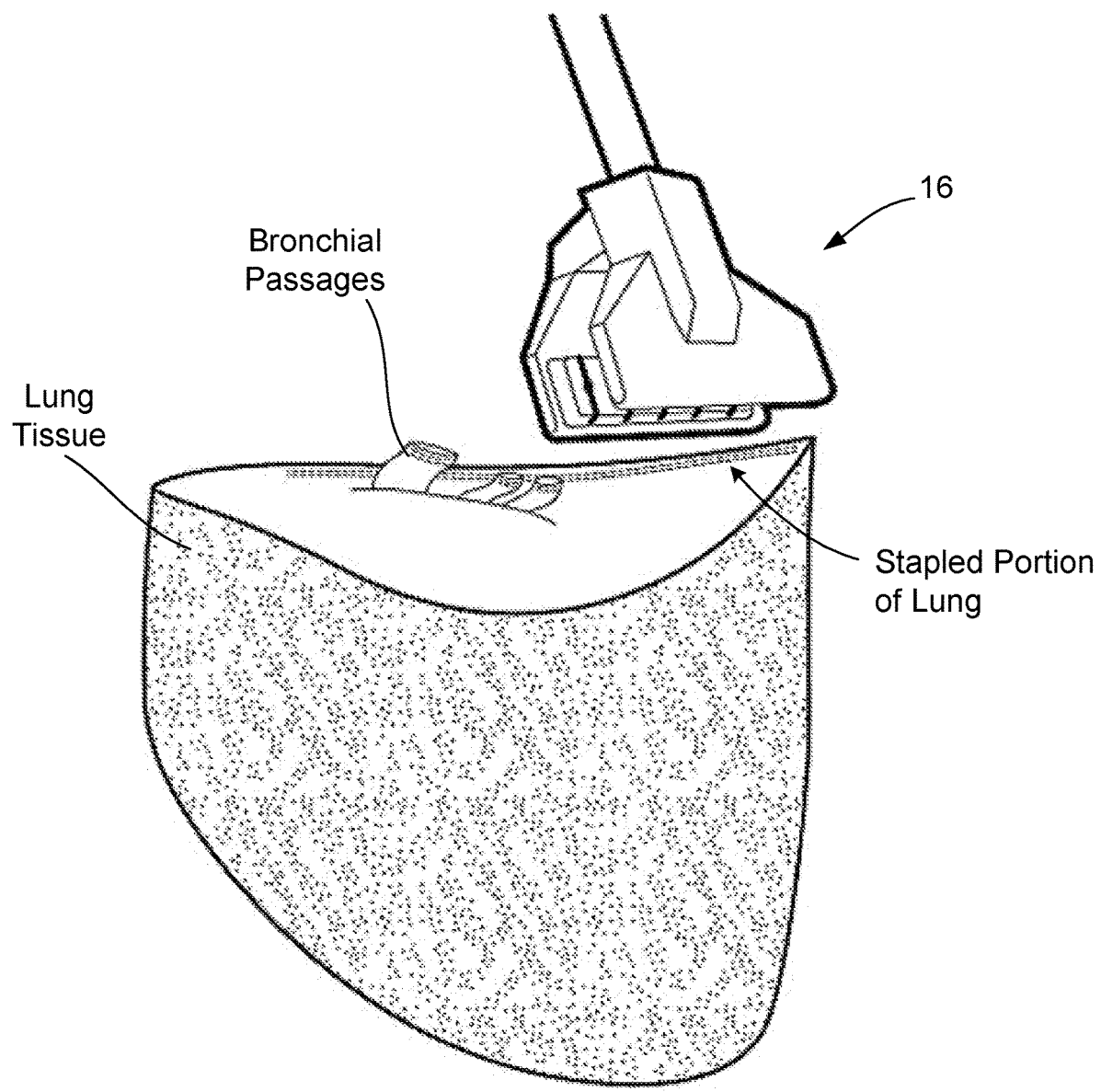
FIG. 8 illustrates positioning of the end effector assembly of FIG. 2 for sealing of a stapled portion of lung tissue (lobe) in an open surgical environment.

FIG. 8 illustrates positioning of the end effector assembly 16 for sealing of a stapled portion of lung tissue (lobe) in an open surgical environment.

Figure 9:
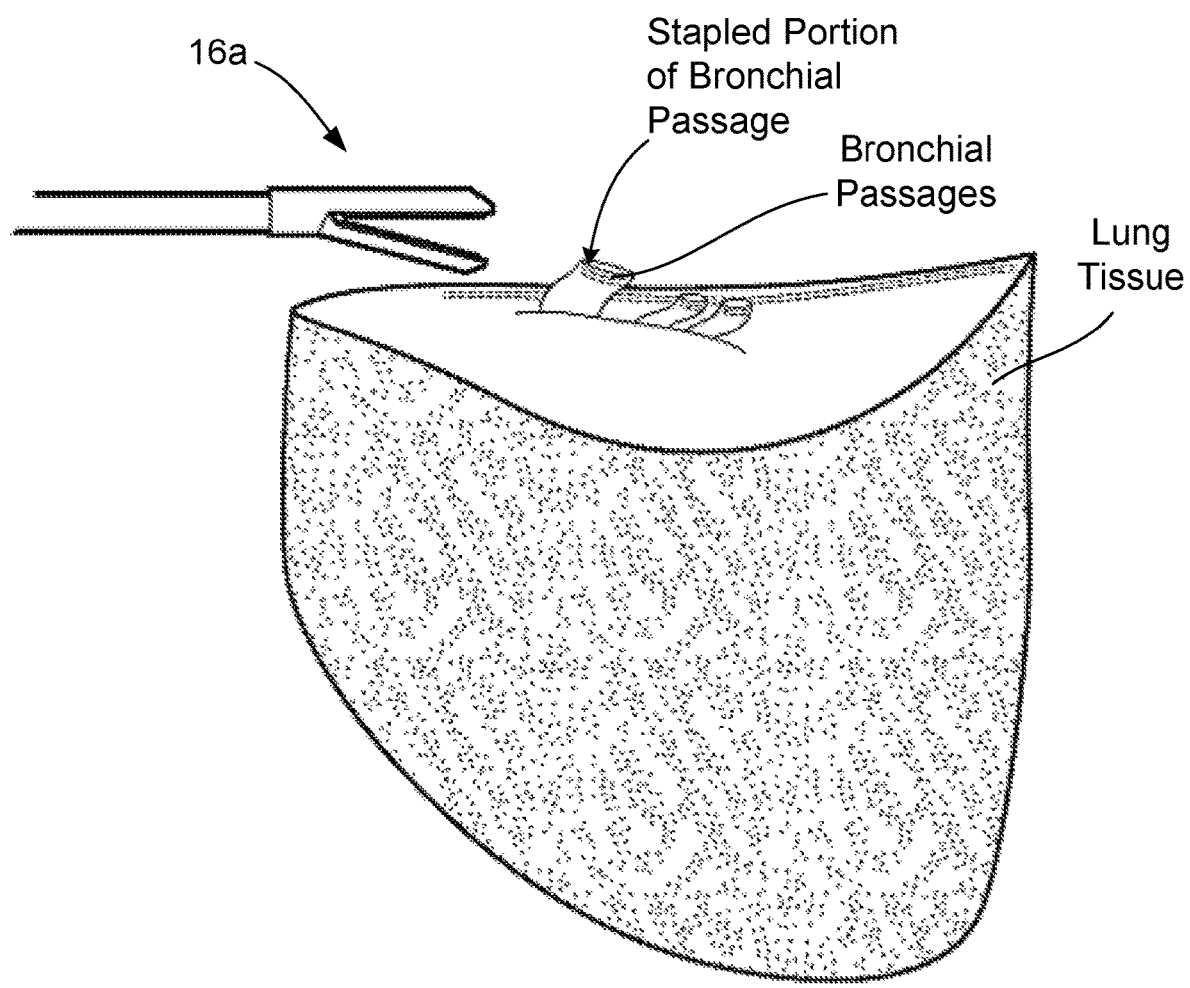
FIG. 9 illustrates positioning of the end effector assembly of FIG. 6 for sealing of a stapled bronchial passageway via laparoscopic procedure.

FIG. 9 illustrates positioning of the end effector assembly 16a for sealing of a stapled bronchial passageway via laparoscopic procedure. As shown, the end effector assembly 16a is configured to laparoscopic procedures, in that the opposing jaws 38a, 38b include atraumatic tips and have a much more narrow profile when compared to the configuration of the end effector assembly 16.

Figure 10A:
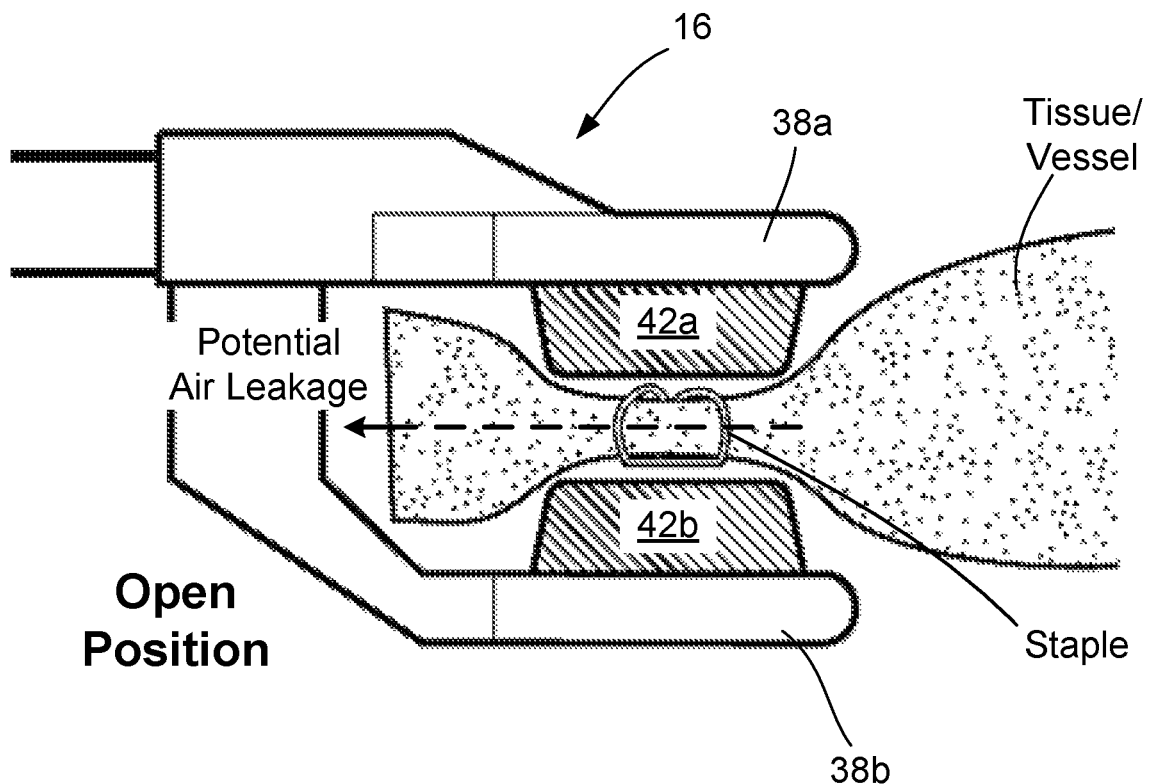
FIGS. 10A and 10B are side views of the end effector assembly of FIG. 2 in open and closed positions, respectively, relative to a portion of stapled lung tissue (FIG. 8), illustrating the cushions of the opposing jaws transitioning from a default shape (FIG. 10A) to a deformed shaped (FIG. 10B) and conforming to the tissue surface and in compliance with the staples.
Figure 10B:
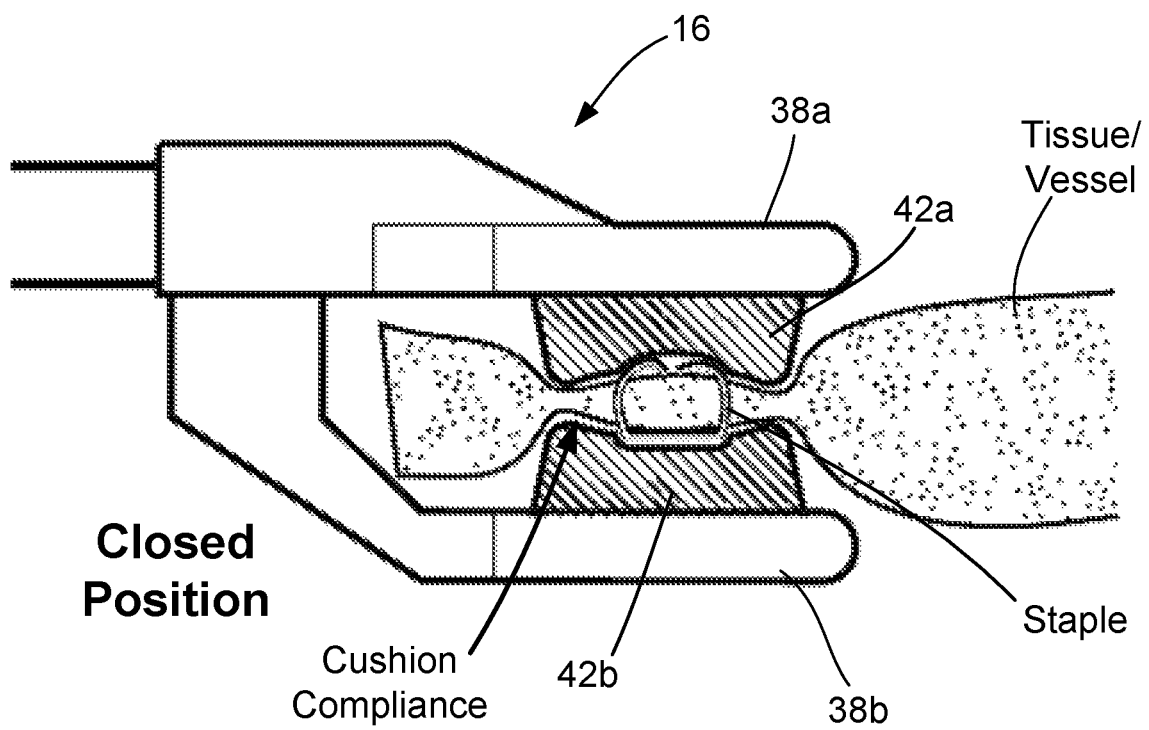

FIGS. 10A and 10B are side views of the end effector assembly 16 in open and closed positions, respectively, relative to a portion of stapled lung tissue (of FIG. 8), illustrating the cushions 42a, 42b of the corresponding opposing jaws 38a, 38b transitioning from a default shape (FIG. 10A) to a deformed shaped (FIG. 10B) and conforming to the tissue surface and in compliance with the staple.

As shown, once a surgeon positions the end effector assembly 16 relative to a target tissue to be sealed, the surgeon may then close the jaws 38a, 38b so as to clamp the target tissue there between. Upon transitioning the opposing jaws 38a, 38b to the closed position, the corresponding cushions 42a, 42b engage opposing sides of the target tissue, including one or more sutures or staples. The surgeon can apply force so as to compress the target tissue between the opposing cushions 38a, 38b, wherein the exterior surface of each cushion 42a, 42b generally conforms to the surface of the tissue and the staple while maintaining the integrity of the staple (i.e., without damaging the staple). Due to the conforming nature of the cushions 38a, 38b, each electrode array 44, specifically the conductive wires 46 is able to come into close contact with, and effectively seal, portions of the target tissue that are immediately adjacent to the staple, which are generally missed with current electrosurgical forceps. As shown, the end effector assembly 16 can generally accommodate an entire cross section of the lung tissue (lobe) to be received between the opposing jaws 38a, 38b.

The surgeon may then activate both the fluid delivery and electrode array 44, each of which can be independently controlled via controller 18, as previously described. The fluid weeping through the perforations 48, to the outer surface of the cushions 42a, 42b is able to carry energy from electrode array 44, thereby creating a virtual electrode. Upon the fluid weeping through the perforations 48, a pool or thin film of fluid is formed on the exterior surface of the cushions 38a, 38b and is configured to seal portions of the target tissue in contact therewith via the RF energy carried from the electrode array 44. Accordingly, the electrosurgical device 14 of the present disclosure provides for complete closure of the target tissue, thereby preventing or reducing the risk of leakage of air, contents, or fluid and subsequently preventing infection or life threatening complications that may otherwise occur with simply a suture or staple closure.

The electrosurgical device of the present disclosure provides numerous advantages. In particular, the electrosurgical device is useful for supplementing an initial closure of a vessel, wound, or incision via suturing or stapling. The deformable cushion on each opposing jaw is configured to deform upon being compressed against the target tissue or vessel and the suture(s) or staple(s) such that the exterior surface of each cushion conforms and corresponds to the tissue or vessel surface and suture(s) or staple(s). The cushion is able to be compressed against the suture or staple without causing physical damage thereto or compromising the structural integrity of the suture or staple. Furthermore, due to the conforming nature of the cushions, each electrode array is able to come into contact with, and effectively seal, portions of the target tissue or vessel that are immediately adjacent to the suture(s) or staple(s), which are generally missed with current electrosurgical forceps as a result of the rigid, non-compliant sealing plates of such forceps. The virtual electrode arrangement of the present device further allows for a non-sticking surface during a sealing procedure, as the saline generally acts as a buffer between the tissue surface and the surface of the conductive wires. Furthermore, the virtual electrode provides for controlled emission of energy, including at least length of elapsed time and intensity, which, in turn, effectively controls the thermal energy released for sealing, which can be consistently maintained between 60° C. and 100° C. to prevent inadvertent damage to surrounding tissue.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications and further embodiments are possible beyond what is shown and described herein. The subject matter herein contains information, exemplification, and guidance that can be adapted to create various other embodiments.

What is claimed is:
1. A method for sealing a portion of tissue or vessels stapled with a staple, the method comprising:
providing a distal end of a device to the portion of tissue or vessels stapled with a staple the device comprising:
a handle including a proximal end and a distal end and at least one lumen extending therethrough; and
an end effector assembly extending from the distal end of the handle, the end effector assembly comprises opposing jaws, at least one of which moves relative to the other, wherein each jaw comprises:
a deformable cushion including a plurality of perforations in communication with the at least one lumen of the handle, the deformable cushion is configured to transition from a default state to a deformed state upon application of a compression force thereto and return to the default state upon removal of the compression force therefrom, wherein the plurality of perforations are configured to allow the passage of a fluid from the lumen of the handle to an exterior surface of the deformable cushion; and
an electrode array comprising a plurality of conductive wires positioned on the exterior surface of the deformable cushion and configured to conduct energy for ablation or coagulation of a stapled portion of a target tissue or vessel, applying compression force to transition the deformable cushion from the default state to the deformed state over the portion of the tissue or vessels; and conducting energy for ablation or coagulation to the portion of tissue or vessels.

2. The method of claim 1, wherein the step of applying compression force to transition the deformable cushion comprises actuating the handle which comprises a trigger configured to control movement of one or both jaws relative to one another between the open and closed positions.

3. The method of claim 2, wherein, in the closed position, the opposing jaws compress the stapled portion of target tissue or vessel there between.

4. The method of claim 3, wherein the exterior surface of the cushion of each jaw is configured to compress inwardly and conform to the surface of the staple and the surface of the target tissue or vessel, to thereby enable sealing of the target tissue or vessel without compromising the structural integrity of the staple or the target tissue or vessel.

5. The method of claim 4, wherein portions of the electrode array are maintained a close distance to portions of the target tissue or vessel on both sides of, and immediately adjacent to, the staple.

6. The method of claim 1, wherein the cushion of each jaw comprises a nonconductive material.

7. The method of claim 1, wherein the cushion of each jaw comprises a shape memory material.

8. The method of claim 1, wherein the cushion of each jaw comprises an elastomeric material.

9. The method of claim 1, further comprising the step of passing a fluid from the lumen of the handle to the exterior surface of the deformable cushion.

10. The method of claim 9, wherein the exterior surface of the cushion of each jaw comprises at least one portion of surface texturing to enhance fluid distribution.

11. The method of claim 9, wherein the step of passing the fluid from the lumen of the handle to the exterior surface of the deformable cushion comprises delivery of fluid to the end effector assembly and through the plurality of perforations on the cushion of each jaw, wherein delivery of the fluid is controllable via a controller.

12. The method of claim 9, wherein the exterior surface of the cushion of each jaw is configured to couple energy from the electrode array with the fluid to provide a non-stick surface when the energy is applied to the target tissue or vessel.

13. The method of claim 9, wherein at least one of the plurality of conductive wires is configured to conduct energy to be carried by fluid passing through the plurality of perforations to the exterior surface of the deformable cushion to thereby provide a virtual electrode arrangement.

14. The method of claim 13, wherein the energy is radiofrequency (RF) energy.

15. The method of claim 13, wherein the fluid is conductive fluid.

16. The method of claim 15, wherein the conductive fluid is saline.

17. The method of claim 1, wherein each opposing jaw comprises an atraumatic distal tip.

18. The method of claim 1, wherein each of the plurality of conductive wires is aligned with a separate respective one of the plurality of perforations.

19. The method of claim 1, wherein each of the plurality of conductive wires, or one or more sets of a combination of conductive wires, is configured to independently receive an electrical current from an energy source and independently conduct energy.

20. The method of claim 19, wherein the plurality of conductive wires are equidistantly spaced apart from one another along a length of the exterior surface of the deformable cushion.

* * * * *